US011511312B2

(12) United States Patent
Dimakos et al.

(10) Patent No.: US 11,511,312 B2
(45) Date of Patent: Nov. 29, 2022

(54) APPLICATORS FOR APPLYING FIBERS TO SURFACES

(71) Applicants: Nick Dimakos, Mississauga (CA); Steven Henry Fyke, Waterloo (CA); Tim MacKay, Kitchener (CA); Alina Oprea, Waterloo (CA)

(72) Inventors: Nick Dimakos, Mississauga (CA); Steven Henry Fyke, Waterloo (CA); Tim MacKay, Kitchener (CA); Alina Oprea, Waterloo (CA)

(73) Assignee: SURETHIK, Mississauga (CA)

( * ) Notice: Subject to any disclaimer, the term of this patent is extended or adjusted under 35 U.S.C. 154(b) by 0 days.

(21) Appl. No.: 16/276,764

(22) Filed: Feb. 15, 2019

(65) Prior Publication Data

US 2019/0255558 A1 Aug. 22, 2019

Related U.S. Application Data

(60) Provisional application No. 62/632,787, filed on Feb. 20, 2018.

(51) Int. Cl.

| | |
|---|---|
| ***B05C 17/005*** | (2006.01) |
| ***B65D 83/00*** | (2006.01) |
| ***B65D 47/04*** | (2006.01) |
| ***A61K 8/02*** | (2006.01) |
| ***B05B 11/06*** | (2006.01) |
| ***A45D 44/00*** | (2006.01) |

(Continued)

(52) U.S. Cl.

CPC ............ *B05C 17/005* (2013.01); *A45D 44/00* (2013.01); *A61K 8/027* (2013.01); *B05B 7/1422* (2013.01); *B05B 7/1486* (2013.01); *B05B 11/061* (2013.01); *B05B 11/062* (2013.01); *B65D 47/04* (2013.01); *B65D 83/0055* (2013.01); *A61K 2800/87* (2013.01); *B05B 7/0081* (2013.01); *B05B 11/0008* (2013.01)

(58) Field of Classification Search

CPC ... B05C 17/005; B05B 11/062; B05B 7/1486; B05B 7/0081; B05B 11/061; B05B 11/0008; B05B 7/1422; A45D 44/00; B65D 83/0055; B65D 47/04; A61K 8/027; A61K 2800/87

See application file for complete search history.

(56) References Cited

U.S. PATENT DOCUMENTS 277,900 A * 5/1883 Hayes .................. B05B 11/062 222/633

471,865 A * 3/1892 Howard .......... A61M 2202/064 604/58

(Continued)

*Primary Examiner* — Frederick C Nicolas

(74) *Attorney, Agent, or Firm* — Bereskin & Parr LLP

(57) ABSTRACT

An applicator for applying fibers to a surface is described herein. The applicator includes a body having a first end and a second end. The first end has a first opening configured to couple to a container housing the fibers and to receive the fibers from the container. The second end has a second opening for dispensing the fibers from the body. The applicator also includes an air flow generating member for creating an air current for propelling the fibers through the second opening as the fibres pass along a pathway between the first opening and the second opening. The fibers are directed along the pathway from the first opening towards the second opening and into the air current by gravity.

8 Claims, 7 Drawing Sheets

(51) Int. Cl.

| | |
|---|---|
| ***B05B 7/14*** | (2006.01) |
| *B05B 7/00* | (2006.01) |
| *B05B 11/00* | (2006.01) |

(56) References Cited

U.S. PATENT DOCUMENTS

| | | | | | |
|---|---|---|---|---|---|
| 576,437 | A * | 2/1897 | Elliott | A61M 3/00 | 604/217 |
| 600,547 | A * | 3/1898 | Mazzanovich | B05B 11/062 | 222/633 |
| 1,142,636 | A * | 6/1915 | Singer | B05B 11/062 | 222/633 |
| 1,755,329 | A * | 4/1930 | McCormack | E04F 21/12 | 239/654 |
| 1,776,489 | A * | 9/1930 | Cobb | B05B 11/062 | 222/633 |
| 1,852,685 | A * | 4/1932 | Tremblay | A45D 33/02 | 222/633 |
| 1,934,793 | A * | 11/1933 | Crain | A61M 31/00 | 604/58 |
| 2,014,671 | A * | 9/1935 | Rothe | B05B 11/06 | 239/362 |
| 2,098,160 | A * | 11/1937 | Perritt | B05B 11/00 | 222/209 |
| 2,122,234 | A * | 6/1938 | McAuliffe | B05B 11/062 | 604/217 |
| 2,358,329 | A * | 9/1944 | Houghton | B05B 11/062 | 222/633 |
| 2,950,564 | A * | 8/1960 | Bonine | B05B 11/062 | 222/631 |
| 3,147,144 | A * | 9/1964 | Kurte | B29C 37/0071 | 118/420 |
| 3,237,819 | A * | 3/1966 | Fillmore | B65D 47/265 | 222/548 |
| 3,320,879 | A * | 5/1967 | Edwards | G03G 15/0877 | 101/335 |
| 3,898,956 | A * | 8/1975 | Andrako | G03G 15/0877 | 399/260 |
| 3,949,909 | A * | 4/1976 | Sterner | A01K 5/008 | 222/199 |
| 3,972,449 | A * | 8/1976 | Smith | B65G 47/19 | 222/64 |
| 3,987,937 | A * | 10/1976 | Goucher | B05B 7/14 | 406/115 |
| 3,999,687 | A * | 12/1976 | Baer | G03G 15/0853 | 399/62 |
| 4,071,169 | A * | 1/1978 | Dunn | B01F 13/0001 | 222/71 |
| 4,109,861 | A | 8/1978 | McHugh | | |
| 4,184,258 | A * | 1/1980 | Barrington | A61C 3/025 | 222/636 |
| 4,238,053 | A * | 12/1980 | Bonini | B67D 3/0009 | 222/129.1 |
| 4,265,065 | A * | 5/1981 | Osada | B65D 88/28 | 222/460 |
| 4,367,988 | A * | 1/1983 | Leong | G01F 11/24 | 222/370 |
| 4,526,493 | A * | 7/1985 | Hall | E01C 19/43 | 404/105 |
| 4,678,377 | A * | 7/1987 | Bouchard | B05B 7/1413 | 222/630 |
| 4,880,161 | A * | 11/1989 | Wright | B05B 11/3052 | 239/330 |
| 5,069,390 | A * | 12/1991 | Stern | B05B 11/062 | 222/325 |
| 5,119,993 | A * | 6/1992 | Gunzel, Jr. | A01C 15/02 | 239/600 |
| 5,143,254 | A * | 9/1992 | Laurent | G01F 11/24 | 222/1 |
| 5,188,295 | A * | 2/1993 | Stern | B05B 11/062 | 222/325 |
| 5,573,149 | A * | 11/1996 | Saito | B05B 7/144 | 222/152 |
| 5,709,322 | A * | 1/1998 | Ricciardi | G01F 13/005 | 222/227 |
| 5,894,960 | A * | 4/1999 | Rodden, Jr. | B05B 11/303 | 222/207 |
| 6,294,216 | B1 * | 9/2001 | Ikezaki | B05B 5/047 | 427/459 |
| 6,616,067 | B1 * | 9/2003 | Hunter | B05B 9/0822 | 222/209 |
| 6,691,892 | B2 * | 2/2004 | Odessa | B05B 11/062 | 222/1 |
| 6,948,535 | B2 * | 9/2005 | Stegemoeller | B65G 65/46 | 141/67 |
| 7,140,522 | B2 * | 11/2006 | Kress | A45D 19/16 | 222/633 |
| 7,455,248 | B2 * | 11/2008 | Kablik | A61L 31/042 | 239/654 |
| 7,997,449 | B2 * | 8/2011 | Banco | B05B 11/3081 | 222/136 |
| 8,172,115 | B1 * | 5/2012 | Mulhauser | B05B 11/061 | 222/633 |
| 8,235,258 | B2 * | 8/2012 | Eastin | A01M 9/00 | 222/412 |
| 8,245,958 | B2 * | 8/2012 | Ko | B05B 11/06 | 239/650 |
| 8,272,584 | B2 | 9/2012 | Barnett et al. | | |
| 8,721,582 | B2 * | 5/2014 | Ji | A61M 11/007 | 604/58 |
| 8,827,980 | B2 * | 9/2014 | Ji | A61M 11/008 | 604/500 |
| 8,870,024 | B2 * | 10/2014 | Mendes | A47F 1/03 | 221/204 |
| 8,985,391 | B2 * | 3/2015 | Ross | B29B 13/022 | 222/1 |
| 9,851,240 | B2 * | 12/2017 | Sollazzo Lee | G01F 11/20 | |
| 9,943,865 | B2 * | 4/2018 | Martiskainen | B05B 11/061 | |
| 2005/0205087 | A1 | 9/2005 | Kablik et al. | | |
| 2005/0230426 | A1 * | 10/2005 | de la Guardia | B05B 9/0822 | 222/207 |
| 2010/0147880 | A1 * | 6/2010 | Kreutzer | C04B 14/30 | 222/55 |
| 2011/0114662 | A1 * | 5/2011 | Saunders | B65G 65/44 | 222/1 |
| 2011/0163183 | A1 * | 7/2011 | Ko | B05B 11/06 | 239/302 |
| 2011/0233306 | A1 * | 9/2011 | Ko | B05B 11/062 | 239/337 |
| 2015/0201732 | A1 * | 7/2015 | Kakon | A45D 33/02 | 222/333 |
| 2016/0018250 | A1 * | 1/2016 | Sollazzo Lee | G01F 11/24 | 222/1 |
| 2016/0243566 | A1 | 8/2016 | Martiskainen et al. | | |
| 2016/0354562 | A1 * | 12/2016 | Morrison | G16H 40/63 | |

* cited by examiner

APPLICATORS FOR APPLYING FIBERS TO SURFACES

CROSS-REFERENCE TO RELATED APPLICATION

This application claims the benefit of U.S. Provisional Patent Application No. 62/632,787, filed Feb. 20, 2018 and the entire content of U.S. Provisional Patent Application No. 62/632,787 is hereby incorporated by reference.

TECHNICAL FIELD

The embodiments disclosed herein relate to applicators and, in particular to applicators for applying fibers to surfaces.

BACKGROUND

Hair thickening fibers can be used to camouflage baldness and improve one's appearance by providing fuller looking hair. Hair thickening fibers are generally shaken directly from a container onto the hair, scalp and/or face where thinning spots appear and adhere to the hair, scalp and/or face to provide fuller looking hair. It can be difficult to achieve natural looking hair as shaking the fibers can lead to uneven coverage of the thinning spots.

Accordingly, there is a need for a new applicator for applying fibers to surfaces.

SUMMARY

This summary is intended to introduce the reader to the more detailed description that follows and not to limit or define any claimed or as yet claimed invention. One or more inventions may reside in any combination or sub-combination of the elements or process steps disclosed in any part of this document including its claims and figures.

According to one broad aspect, an applicator for applying fibers to a surface is provided. The applicator includes a body having a first end and a second end. The first end has a first opening configured to couple to a container housing the fibers and to receive the fibers from the container. The second end has a second opening for dispensing the fibers from the body. The applicator also includes an air flow generating member for creating an air current for propelling the fibers through the second opening as the fibres pass along a pathway between the first opening and the second opening. The fibers are directed along the pathway from the first opening towards the second opening and into the air current by gravity.

The second opening may be perpendicular to the first opening.

The air flow generating member may be a bulb and may be configured to create the air current upon an outer wall of the bulb being depressed.

The bulb may be configured to create the air current upon the outer wall of the bulb being depressed in a direction towards the pathway.

The air flow generating member includes an inlet valve for directing air into the air flow generating member and an outlet valve for directing air out of the air flow generating member.

The applicator may also include a perforated surface positioned along the pathway between the first opening and the second opening, the perforated surface having perforations that are sized and shaped to provide for selective passage of the fibres through the perforated surface.

The perforations may be sized and shaped to provide for passage of at least a portion of the fibres through the perforated surface and into the air current in response to agitation of the body, the fibres being directed through the perforated surface and into the air current by gravity.

The perforated surface may be horizontally oriented and vertically spaced from the air current to support at least a portion of the fibers above the air current.

The perforated surface may be oriented to have an acute angle relative to a bottom surface of the body and is vertically spaced from the air current to support at least a portion of the fibers above the air current.

The perforated surface may be vertically oriented and vertically spaced from the air current to support at least a portion of the fibers above the air current.

The perforated surface may be vertically oriented and positioned within the air current to inhibit passage of the fibres through the second opening in the absence of the air current.

The applicator may also include a second perforated surface vertically oriented and positioned within the air current to inhibit passage of the fibres into the air flow generating member in the absence of the air current.

The body may also include a chamber positioned along the pathway between the first opening and the second opening, the chamber including a perforated surface for retaining the fibers in the chamber.

The applicator may also include a vibrator positioned adjacent to the chamber, the vibrator configured to agitate the chamber to provide for passage of the fibres through the perforated surface.

The vibrator may directly agitate the chamber to provide for passage of the fibres through the perforated surface.

The vibrator may agitate a pathway member positioned adjacent to the chamber to provide for passage of the fibres through the perforated surface.

The pathway member may be positioned adjacent to the chamber and below the perforated surface to receive the fibres as they fall through the perforated surface.

The pathway member may be positioned adjacent to the chamber and above the air current to direct the fibres into the air current as they pass through the pathway.

The applicator may also include a power source to provide power to the vibrator.

The fibers may be hair thickening fibers.

Other aspects and features will become apparent, to those ordinarily skilled in the art, upon review of the following description of some exemplary embodiments.

BRIEF DESCRIPTION OF THE DRAWINGS

The drawings included herewith are for illustrating various examples of articles, methods, and apparatuses of the present specification. In the drawings.

Figure 1:
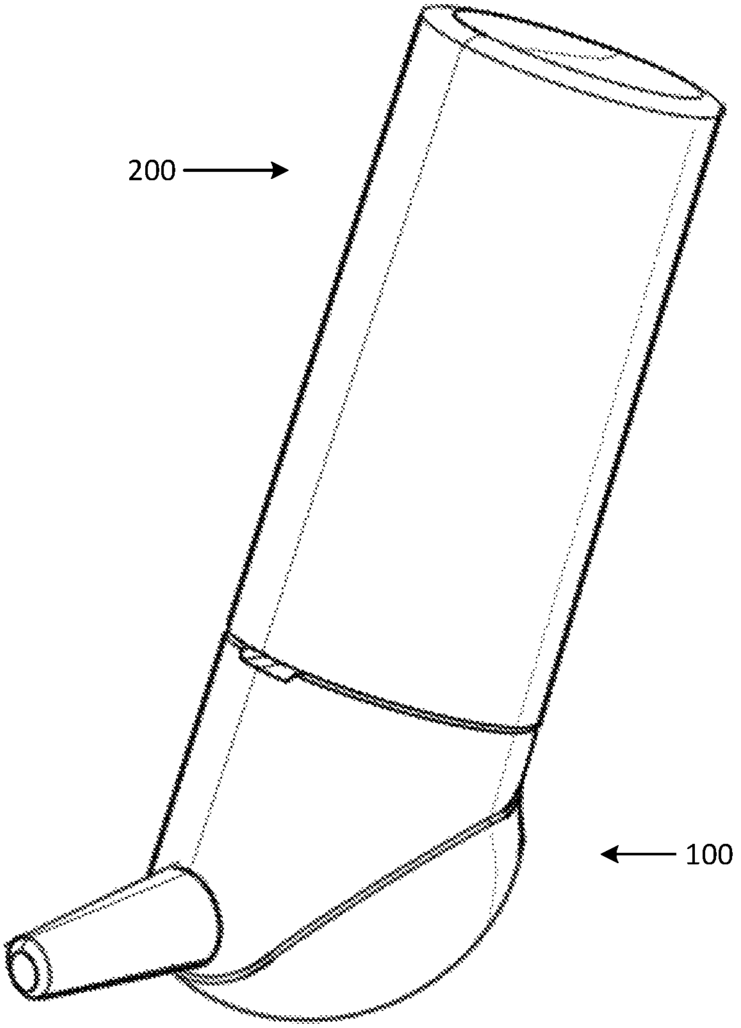
FIG. 1 is a perspective view of an applicator for applying hair thickening fibers, according to one embodiment.

The drawings included herewith are for illustrating various examples of articles, methods, and apparatuses of the teaching of the present specification and are not intended to limit the scope of what is taught in any way.

DETAILED DESCRIPTION

Various apparatuses or processes will be described below to provide an example of each claimed embodiment. No embodiment described below limits any claimed embodiment and any claimed embodiment may cover processes or apparatuses that differ from those described below. The claimed embodiments are not limited to apparatuses or processes having all of the features of any one apparatus or process described below or to features common to multiple or all of the apparatuses described below.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Terms of degree such as “about” and “approximately” as used herein mean a reasonable amount of deviation of the modified term such that the end result is not significantly changed. These terms of degree should be construed as including a deviation of at least ±5% or at least ±10% of the modified term if this deviation would not negate the meaning of the word it modifies.

The terms “an embodiment,” “embodiment,” “embodiments,” “the embodiment,” “the embodiments,” “one or more embodiments,” “some embodiments,” and “one embodiment” mean “one or more (but not all) embodiments of the present invention(s),” unless expressly specified otherwise.

The terms “including,” “comprising” and variations thereof mean “including but not limited to,” unless expressly specified otherwise. A listing of items does not imply that any or all of the items are mutually exclusive, unless expressly specified otherwise. The terms “a,” “an” and “the” mean “one or more,” unless expressly specified otherwise.

As used herein and in the claims, two or more parts are said to be “coupled”, “connected”, “attached”, or “fastened” where the parts are joined or operate together either directly or indirectly (i.e., through one or more intermediate parts), so long as a link occurs. As used herein and in the claims, two or more parts are said to be “directly coupled”, “directly connected”, “directly attached”, or “directly fastened” where the parts are connected in physical contact with each other. None of the terms “coupled”, “connected”, “attached”, and “fastened” distinguish the manner in which two or more parts are joined together.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

Finally, although hair thickening fibers are used as an exemplary material to describe various embodiments of applicators below, the skilled person will understand that the applicators described herein can be used to apply any fibrous material.

Referring to FIG. 1, illustrated therein is a perspective view of an applicator 100 for applying hair thickening fibers. Applicator 100 is configured to couple to a container 200 that houses a fibrous material such as but not limited to hair thickening fibres.

Figure 2:
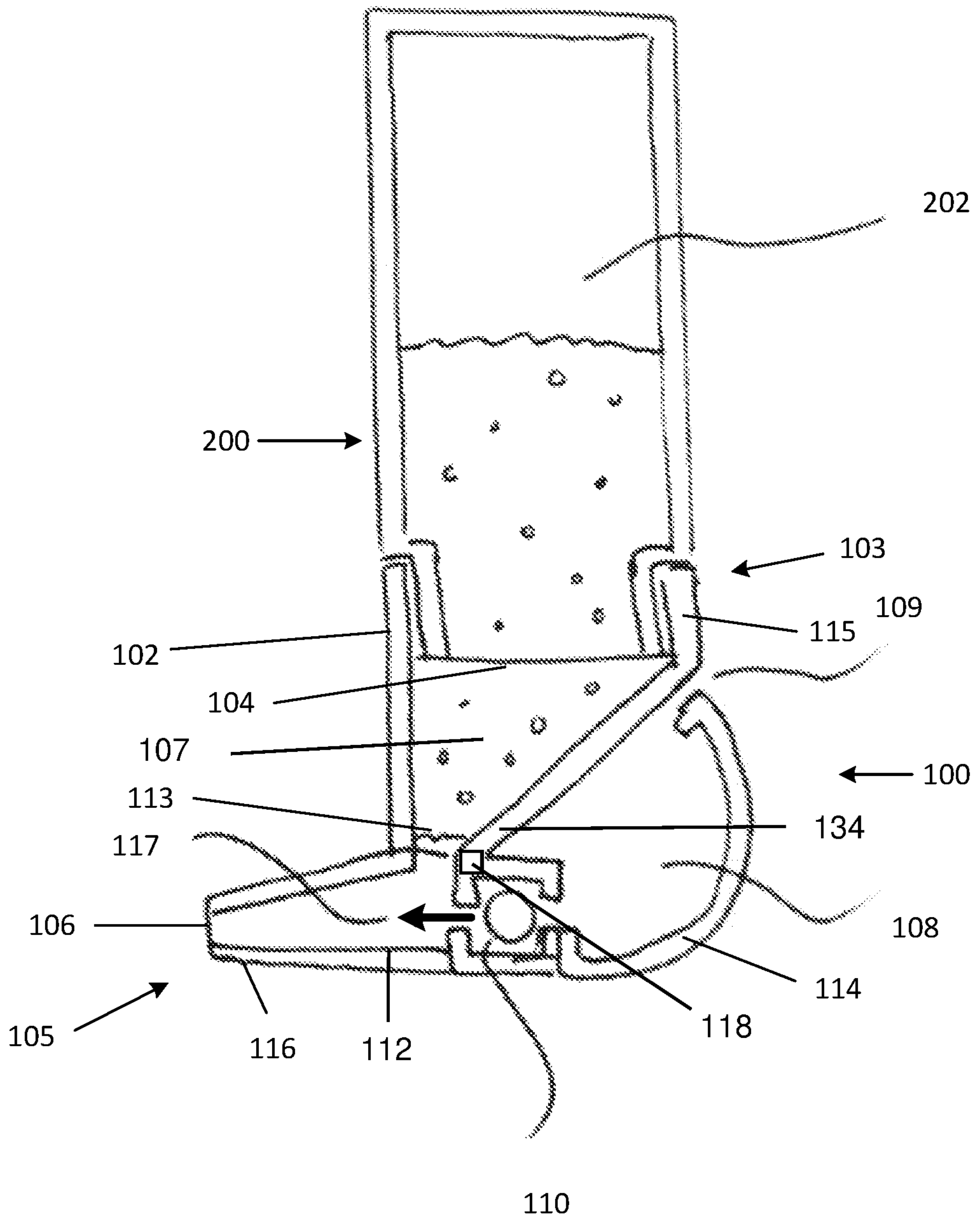
FIG. 2 is a side view of the applicator shown in FIG. 1 shown coupled to a container.

As shown in FIG. 2, applicator 100 has a body 102 having a first (e.g. inlet) end 103 having a first opening 104 configured to couple (e.g. releasably) to a container 200 housing a fibrous material 202 (such as but not limited to hair thickening fibers). In the embodiments shown in the drawings, body 102 is configured to couple to container 200 when container 200 is inverted. Accordingly, hair thickening fibers 202 are fed by gravity from the container 200 into applicator 100. Herein, the term “inverted” refers to an orientation of container 200 when hair thickening fibers 202 contained therein are removed therefrom by gravity. In one embodiment, body 102 is configured to threadingly engage with container 200 when container 200 is inverted.

Body 102 also has a second (e.g. outlet) end 105 opposed to first end 103 having a second opening 106 configured to direct the hair thickening fibers out of the body 102. Second end 105 is positioned downstream of first end 103 so that hair thickening fibers 202 enter applicator 100 at first end 103 and flow through a pathway 107 of body 102 between first end 103 and second end 105 and then are dispensed from the body 102 through second opening 106 of second end 105. In the embodiments shown in the drawings, second opening 106 is configured to be substantially perpendicular to first opening 104. For example, in the embodiments shown in the drawings, hair thickening fibers 202 are fed from the container into body 102 by gravity, are directed from the first opening 104 towards the second opening 106 through the body 102 along pathway member 134 along the pathway 107 in a substantially downward direction by gravity, and are dispensed (e.g. propelled) through opening 106 in a substantially horizontal direction by the air flow generating member 108.

Body 102 also has an air flow generating member 108. Air flow generating member 108 can be any means of generating a flow of air, including but not limited to a fan, a bulb, an opening that provides for a person to blow air into the body 102, etc. In the embodiments shown in FIGS. 1-5, air flow generating member 108 has an inlet 109 and an outlet 110. In some embodiments, such as that shown in FIG. 3, inlet 109 may be configured as a first (e.g. inlet) valve 309 that provides for air to enter the air flow generating member 108 and inhibits air from exiting the air flow generating member 108. In some embodiments, outlet 110 may configured as a second (e.g. outlet) valve 110 that provides for air to exit the air flow generating member 108 and inhibits air from entering the air flow generating member 108. Air flow generating member 108 is configured to direct air from the environment into body 102 at a position along pathway 107 between first opening 104 and second opening 106 to propel hair thickening fibers 202 out of body 102. Although the term "air" is used throughout this description, the skilled person will understand that any gaseous substance can be used in place of air to propel the hair thickening fibers 202 from applicator 100.

In the embodiment shown in FIG. 1, air flow generating member 108 is a hollow bulb formed of an elastic, resilient material disposed on and attached to the second end 105 of the body 102 opposite the first end 103 to which the container 200 is attachable.

Air flow generating member 108 has an opening generally aligned with second opening 106 and is in fluidic communication with passageway 107 so that when an outer wall 114 of air flow generating member 108 is depressed in a direction towards pathway 107, a current of air (shown as arrow 117) is expelled from air flow generating member 108 and passes in a substantially straight line through second valve 110 to the passageway 107. The current of air 117 expelled from the air generating member 108 may strike the hair thickening fibers 202 when the hair thickening fibers 202 are resting on an inner surface 112 of an outer wall 116 when container 200 is attached to the applicator 100 and the hair thickening fibers 202 have been gravity fed into the applicator 100. Upon striking one or more of the surface 112 and the hair thickening fibers 202, the current of air 117 from air flow generator 108 creates an air suspension of the hair thickening fibers 202 that passes out of the second opening 106 to propel the hair thickening fibers 202 out of the applicator 100. In the embodiment shown in FIG. 3, applicator 300 is shown where inner surface 312 is curved (e.g. convex) to inhibit hair thickening fibers resting thereon from passing through the opening 104 under the influence of gravity.

Body 102 may include a perforated surface 113 positioned within pathway 107. Perforated surface 113 includes perforations (not shown) sized and shaped to provide for the selective passage of hair thickening fibers 202 through the perforated surface 113. For instance, perforated surface 113 can be a grate, a membrane or any material that provides perforations for the selective passage of hair thickening fibers 202 there though. In some embodiments, perforated surface 113 may be horizontally oriented and vertically spaced from the air current to support hair thickening fibers 202 above the air current created by the air flow generating member 108. In some embodiments, perforations of the perforated surface 113 may be configured to support at least a portion of the hair thickening fibers 202 above the air current created by the air flow generating member 108 and provide for at least a portion of the hair thickening fibers 202 to pass through the perforated surface 113 upon agitation of body 102 (e.g. mechanical agitation such as but not limited to manual shaking by a user of the applicator) and fall via gravity either directly into the air current or onto surface 112 to be struck by the current of air created by air flow generating member 108 and propelled out of second opening 106. Agitation may be provided by any appropriate means, such as but not limited to manual shaking of the applicator 100 by a user or direct agitation of the perforated surface 113 by a vibrator 118 positioned within the body 102.

Second valve 110 is a one-way air injecting valve that opens during dispensing and closes during refill of air flow generating member 108 to create the current of air and direct the current of air into pathway 107.

Figure 3:
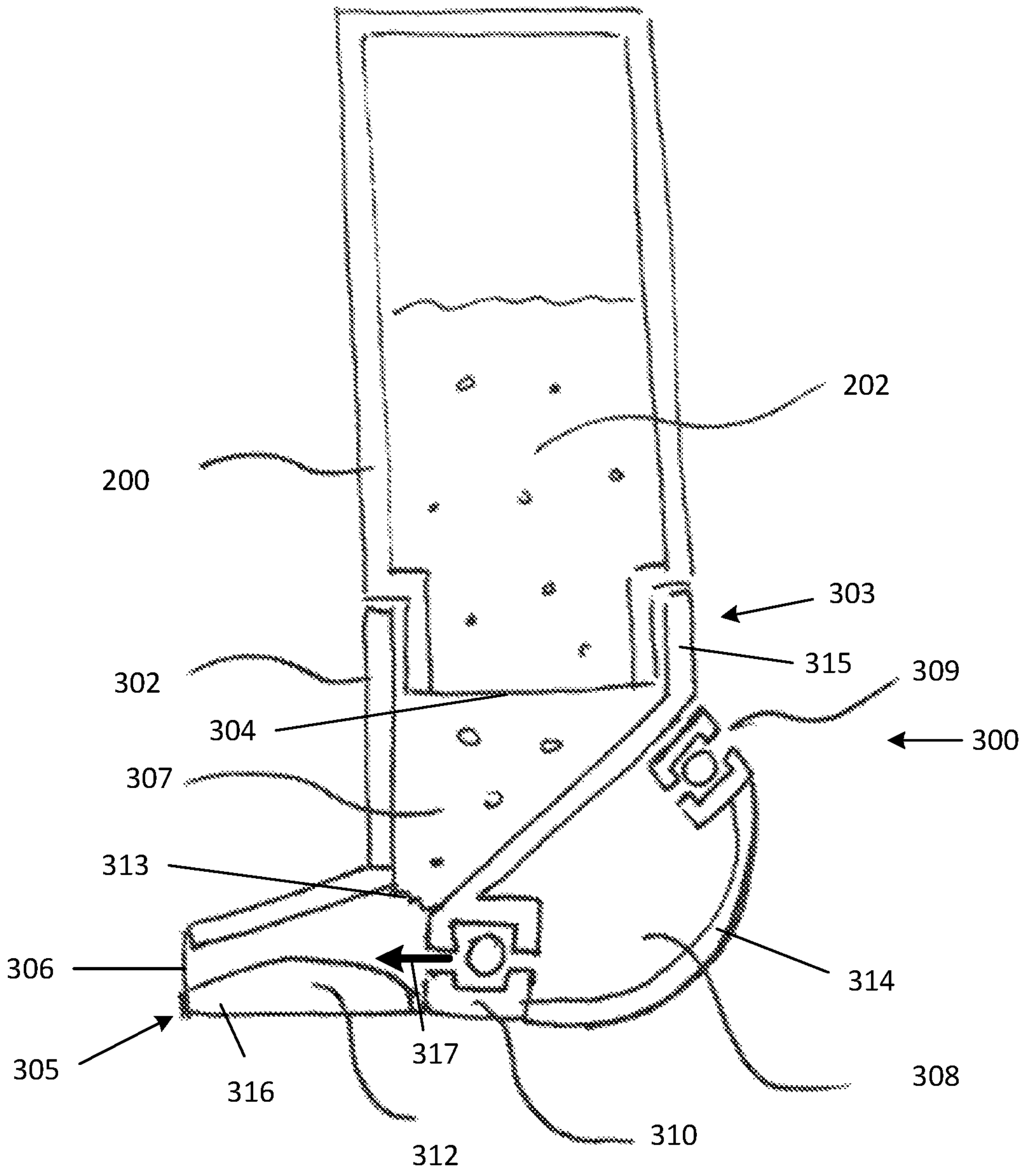
FIG. 3 is a side view of an applicator for applying hair thickening fibers shown coupled to a container, according to another embodiment.

Referring now to FIG. 3, another example applicator 300 is illustrated. Certain elements of the applicator 300 that are similar to those in applicator 100 are referred to using like reference numerals, incremented by 200. To avoid repetition, the similar elements are not discussed in as much detail. Unless otherwise stated below, all the teachings disclosed herein with relation to the applicator 100 can apply to the applicator 300 as well.

In the embodiment shown in FIG. 3, first valve 309 is a one-way injecting valve that opens during refilling and closes during dispensing of air flow generating member 308 to provide for air to enter the air flow generating member 308.

The volume of air held within air flow generating member 108 will corresponds directly to the volume of the current of air created by air generating member 108 that carries the hair thickening fibers out of applicator 100. The volume of air held in air flow generating member is determined by the size and shape of an outer wall 114 of air flow generating member 108. As described above, outer wall 114 of air flow generating member 108 is sized and shaped to be depressed inwardly towards pathway 107 to create a current of air. In the embodiment shown in FIG. 2, outer wall 114 is configured to be substantially aligned with an outer vertical wall 115 of first end 103 and an outer horizontal wall 116 of second end 105.

In this embodiment, applicator 300 includes a perforated surface 313 positioned within pathway 307 between first opening 304 and second opening 306. Perforated surface 313 is vertically spaced above air current 317 and oriented to have an acute angle (i.e. less than 90 degrees) when measured relative to surface 316 and inhibits hair thickening fibers 202 from passing out of second opening 306 prior to creation of the current of air 417.

Figure 4:
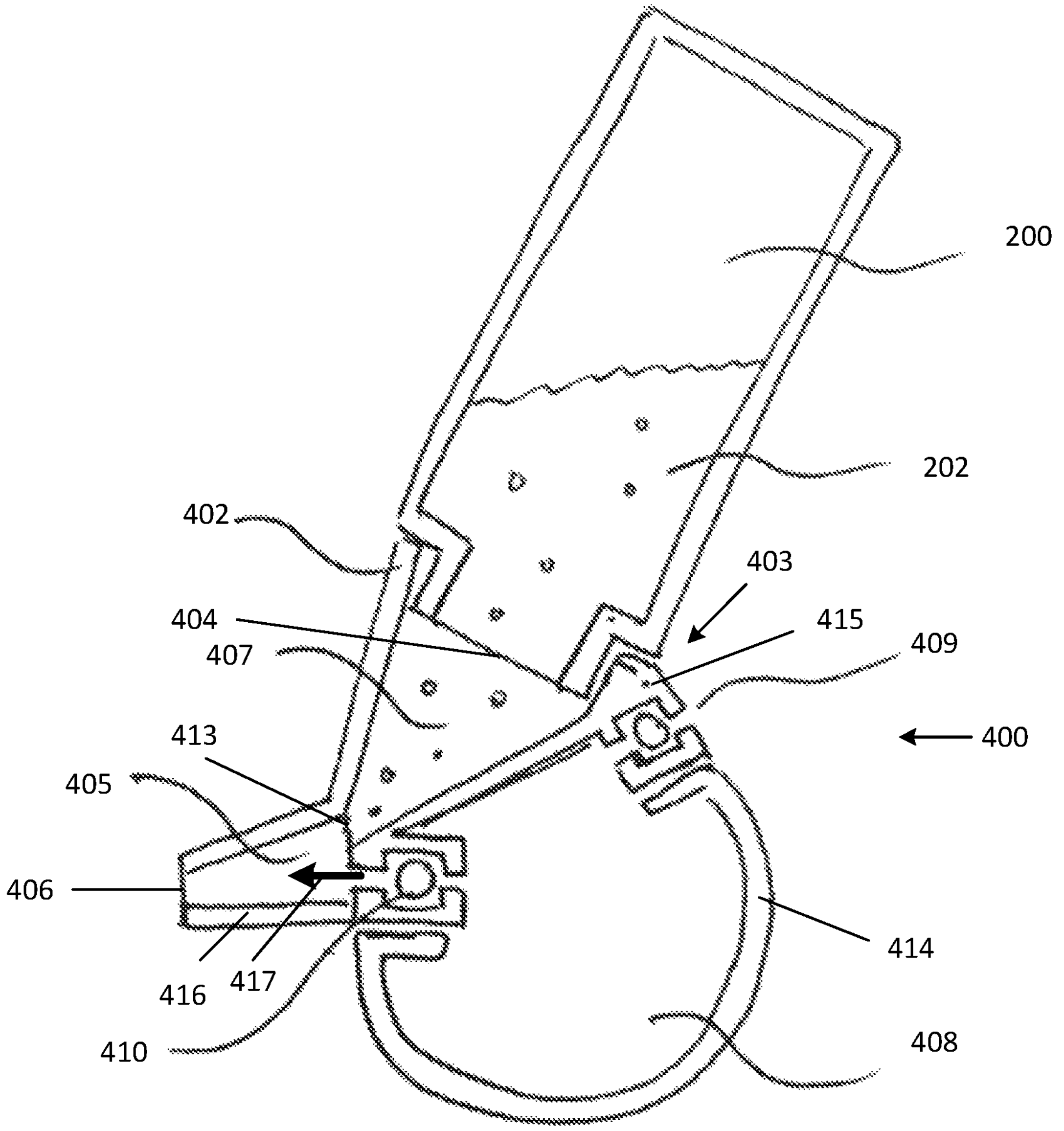
FIG. 4 is a side view of an applicator for applying hair thickening fibers shown coupled to a container, according to another embodiment.

Referring now to FIG. 4, illustrated therein is another embodiment of an applicator 400 for applying fibers to surfaces. Certain elements of the applicator 400 that are similar to those in applicator 100 are referred to using like reference numerals, incremented by 300. To avoid repetition, the similar elements are not discussed in as much detail. Unless otherwise stated below, all the teachings disclosed herein with relation to the applicator 100 or applicator 300 can apply to the applicator 400 as well.

In FIG. 4, air flow generating member 408 is a hollow bulb of elastic, resilient material disposed on and attached to the second end 405 of the body 402 opposite the first end 403 to which the container 200 is attachable, as was shown in FIG. 2. However, in FIG. 4 outer wall 414 of air flow generating member 408 is configured to extend beyond at least one of outer vertical wall 415 of first end 403 and outer horizontal wall 416 of second end 405 to increase a volume of the member 408 when compared to the embodiments of FIGS. 1-3. Accordingly, comparatively, the current of air created by depressing outer wall 414 of applicator 400 has a greater volume than the current of air created by depressing outer wall 114 of applicator 100 and applicator 300.

In this embodiment, applicator 400 includes a perforated surface 413 positioned within pathway 407 between first opening 404 and second opening 406. Perforated surface 413 is vertically oriented to inhibit hair thickening fibers 202 from passing out of second opening 406 prior to creation of the current of air 417.

Figure 5:
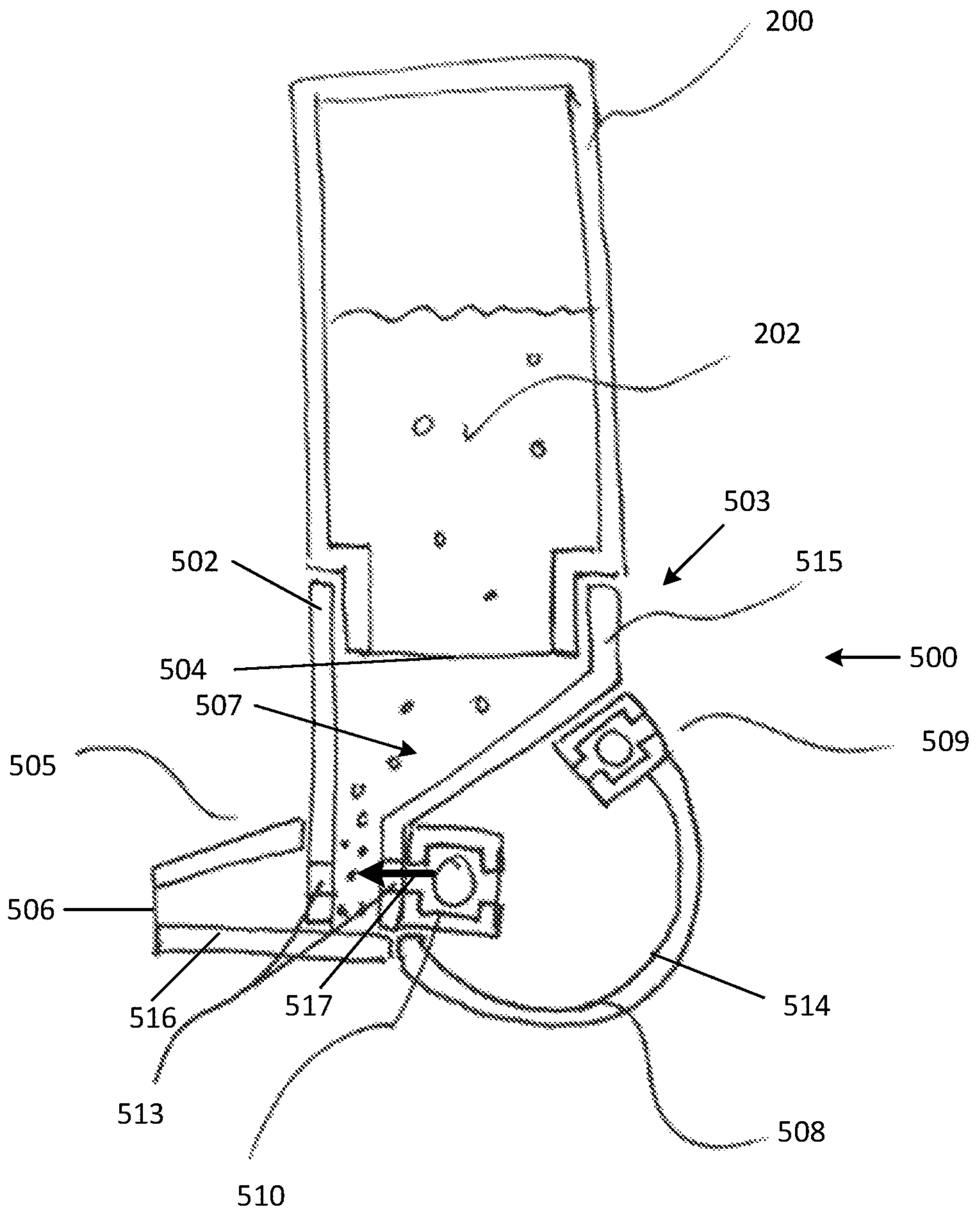
FIG. 5 is a side view of an applicator for applying hair thickening fibers shown coupled to a container, according to another embodiment.

Referring now to FIG. 5, illustrated therein is another embodiment of an applicator 500 for applying fibers to surfaces. Certain elements of the applicator 500 that are similar to those in applicator 100 are referred to using like reference numerals, incremented by 400. To avoid repetition, the similar elements are not discussed in as much detail. Unless otherwise stated below, all the teachings disclosed herein with relation to the applicators 100, 300 or 400 can apply to the applicator 500 as well.

In FIG. 5, applicator 500 has one or more perforated surface 513 that is arranged within pathway 507 to support hair thickening fibers 202 and inhibit passage of air thickening fibers 202 from passing out of second opening 506 prior to creation of the current of air 517. In the embodiment shown, applicator 500 includes two perforated surfaces 513. Perforated surfaces 513 are each vertically arranged and positioned adjacent to surface 516 to provide for fibres 202 from container 200 to fall uninhibited via gravity out of the container 200, through opening 504, along pathway 507 and land on surface 516. In the embodiment shown, perforated surfaces 513 are poisoned on either side of the fibres 202 as they sit on surface 516. One of perforated surfaces 513 is configured to inhibit passage of the fibers 202 into second valve 510 and air generating member 508 and one of perforated surfaces 513 is configured to inhibit passage of fibres 202 out of opening 506 prior to the creation of air current 517. In this embodiment, at least one of the perforated surfaces 513 is arranged in the air current 517.

In the embodiment of FIG. 5, upon creation of the current of air 517, current of air 517 is expelled from air flow generating member 508 and passes in a substantially straight line through second valve 510 to the passageway 507. The current of air 517 expelled from the air generating member 508 strikes the hair thickening fibers 202 sitting directly in front of second valve 510 and creates an air suspension of the hair thickening fibers 202 to propel the hair thickening fibers 202 through one of the perforating surfaces 513 and out of the applicator 500 through second opening 506. Accordingly, in this embodiment, mechanical agitation of the applicator 500 prior to depressing air flow generating member 508 may not be necessary to propel the fibres 202 through the second opening 506.

Figure 6:
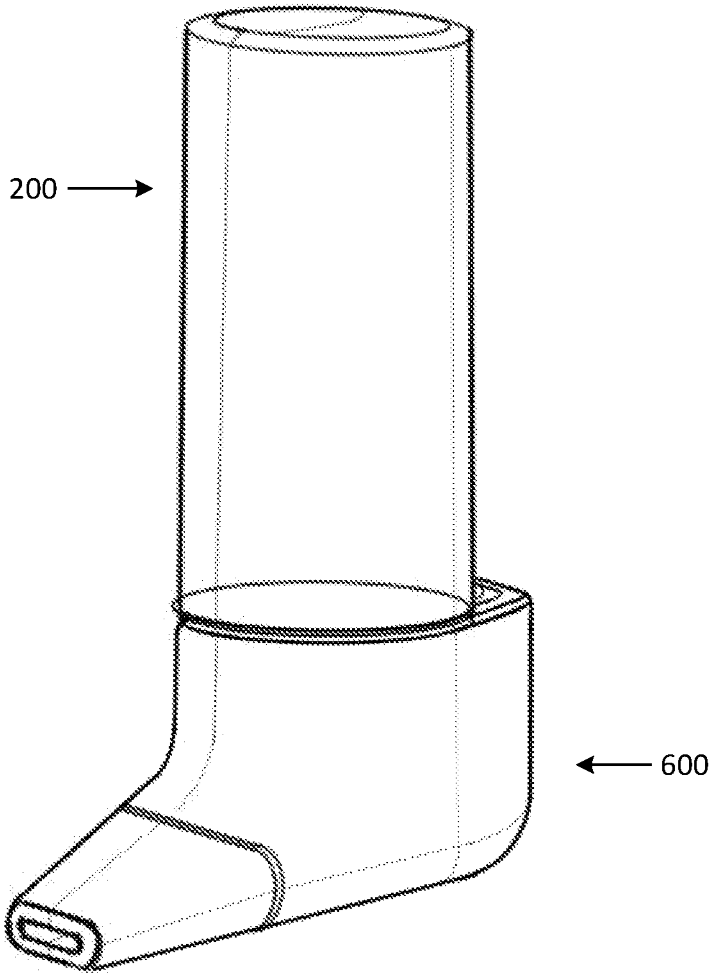
FIG. 6 is perspective view of an applicator for applying hair thickening fibers, according to another embodiment.

FIG. 6 shows a perspective view of an applicator 600 for applying hair thickening fibers. Applicator 600 is configured to couple (e.g. releasably) to a container 200 that houses a fibrous material such as but not limited to hair thickening fibres. Certain elements of the applicator 600 that are similar to those in applicator 100 are referred to using like reference numerals, incremented by 500. To avoid repetition, the similar elements are not discussed in as much detail. Unless otherwise stated below, all the teachings disclosed herein with relation to the applicator 100, 300, 400 and 500 can apply to the applicator 600 as well.

Figure 7:
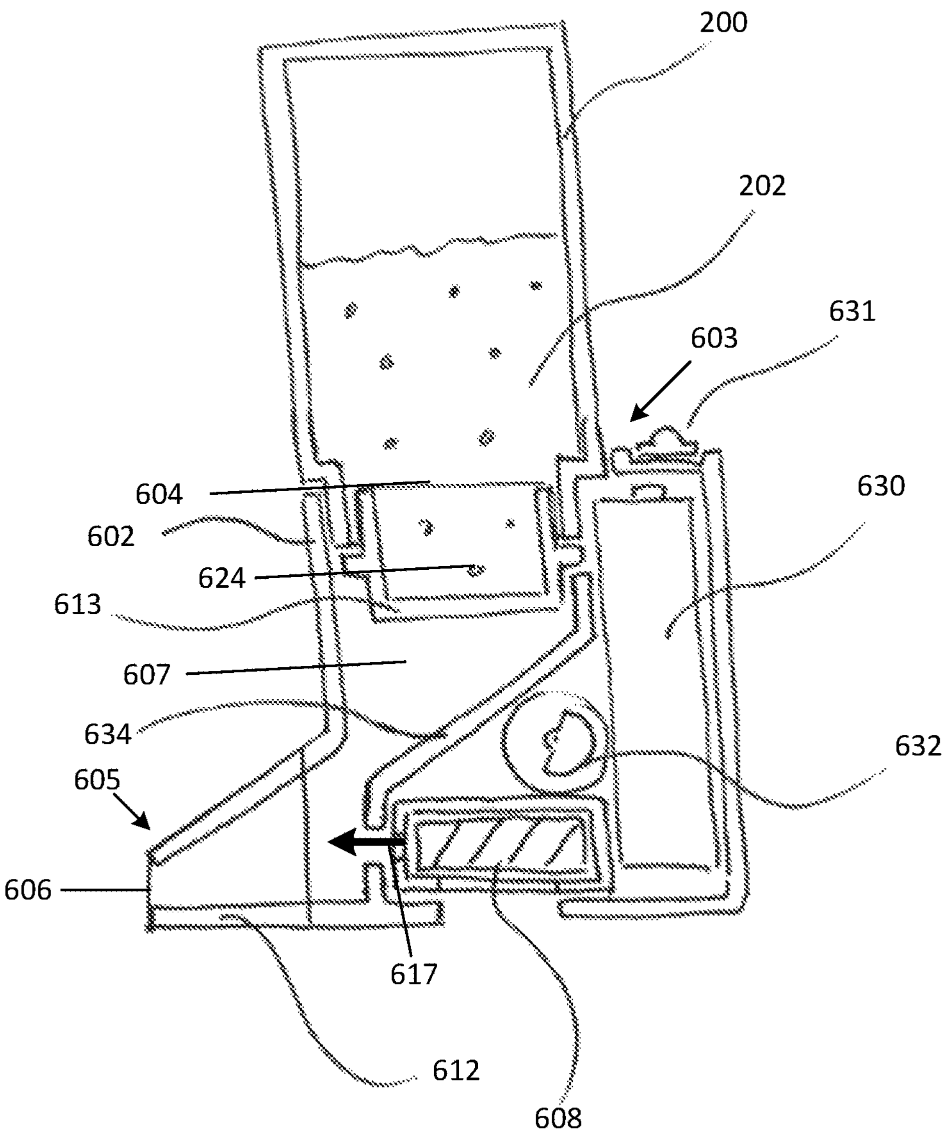
FIG. 7 is a side view of the applicator shown in FIG. 6 shown coupled to a container.

As shown in FIG. 7, applicator 600 has a body 602 having a first (e.g. inlet) end 603 having a first opening 604 configured to couple to a container 200 housing hair thickening fibers 202. In the embodiments shown in the drawings, body 602 is configured to couple to container 200 when container 200 is inverted. Accordingly, hair thickening fibers 202 are fed by gravity from the container 200 into applicator 600.

Body 602 also has a second (e.g. outlet) end 605 opposed to first end 603 having a second opening 606 configured to direct the hair thickening fibers out of the body 602. Second end 605 is positioned downstream of first end 603 so that hair thickening fibers 202 enter applicator 600 at first end 603 and flow through a pathway 607 of body 602 between first end 603 and second end 605 and then are dispensed from the body 602 through second opening 606 of second end 605. Second opening 606 is configured to be substantially perpendicular to first opening 604. Hair thickening fibers 202 are fed by gravity into body 602 in a substantially downward direction and are dispensed through opening 606 in a substantially horizontal direction.

Body 602 also has an air flow generating member 608. Air flow generating member 608 injects air from the environment into body 602 at a position along pathway 607 between first opening 604 and second opening 606 to propel hair thickening fibers 202 out of body 102. In the embodiment shown in FIGS. 6 and 7, air flow generating member 608 is a DC fan. To provide power to at least the DC fan, applicator 600 can have a power source 630 (e.g. batteries).

In the embodiments shown in FIGS. 6 and 7, body 602 also has a hopper 624 positioned at first end 602 adjacent to opening 604. Hopper 624 is configured to support hair thickening fibers 202 received through opening 603 from inverted container 200. Hopper 624 may have a perforated surface 613 configured to selectively provide for passage of hair thickening fibers 202 there through upon mechanical agitation.

When the hair thickening fibers 202 pass through the perforated surface 613 and second opening 606 to be dispensed from applicator 600, hopper 624 can be refilled either by gravity (e.g. the hair thickening fibers 202 falling directly from the container 200), or by a slight mechanical agitation (e.g. vibration) of hopper 624. Mechanical agitation of hopper 624 may also encourage the hair thickening fibers 202 to evenly settle within the hopper 624.

Mechanical agitation can be provided by any appropriate mechanical means, such as but not limited to vibrator 632. As shown in FIG. 7, vibrator 632 can be positioned downstream of hopper 624. In other embodiments, vibrator 632 can be positioned upstream of hopper 624.

In the embodiment shown in FIG. 7, vibrator 632 is positioned to directly vibrate pathway member 634 that directs the hair thickening fibers 202 along pathway 607 towards second outlet 606.

In some embodiments, vibrator 632 vibrating pathway member 634 may also encourage hair thickening fibers 202 passing through perforated surface 613 to evenly distribute across vibrating member 634 prior to passing into the air current 617, Vibrator 632 may also be positioned to directly agitate (e.g. vibrate) at least a portion of hopper 624.

In one embodiment, the vibrator 632 can be a weighted motor. Vibrator 632 can also be powered by power source 630. Other examples of vibrator 632 may include but not limited to a linear actuator, a solenoid that "taps" the side of the chamber, a sieve-type action or any other mechanism for agitating hair thickening fibers 202.

While the above description provides examples of one or more apparatus, methods, or systems, it will be appreciated that other apparatus, methods, or systems may be within the scope of the claims as interpreted by one of skill in the art.

What is claimed is:

1. An hand-held applicator for applying fibers to a surface, the applicator comprising:

a body having a first end and a second end, the first end having a first opening configured to couple to a container housing the fibers and to receive the fibers from the container, the second end having a second opening for dispensing the fibers from the body;

an air flow generating member for creating an air current for propelling the fibers through the second opening as the fibers pass along a pathway between the first opening and the second opening, the fibers being directed along a pathway member positioned within the body and above the air current from the first opening towards the second opening and into the air current; and a vibrator positioned within the body and adjacent to the pathway member and configured to mechanically agitate the pathway member within the body to encourage the fibers to fall into the air current.

2. The applicator of claim 1, wherein the second opening is perpendicular to the first opening.

3. The applicator of claim 1, wherein the air flow generating member is a bulb and is configured to create the air current upon an outer wall of the bulb being depressed.

4. The applicator of claim 3, wherein the bulb is configured to create the air current upon the outer wall of the bulb being depressed in a direction towards the pathway.

5. The applicator of claim 1, wherein the applicator further comprises a perforated surface positioned along the pathway between the first opening and the second opening, the perforated surface having perforations that are sized and shaped to provide for selective passage of the fibers through the perforated surface.

6. The applicator of claim 5, wherein the perforations are sized and shaped to provide for passage of at least a portion of the fibers through the perforated surface and into the air current in response to agitation of the body, the fibers being directed through the perforated surface and into the air current by gravity.

7. The applicator of claim 6, wherein the perforated surface is horizontally oriented and vertically spaced from the air current to support at least a portion of the fibers above the air current.

8. The applicator of claim 1, wherein the fibers are hair thickening fibers.

* * * * *